(12) United States Patent
Ito

(10) Patent No.: US 6,561,985 B2
(45) Date of Patent: May 13, 2003

(54) AUTOMATIC BLOOD-PRESSURE MEASURING APPARATUS

(75) Inventor: Hisashi Ito, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/985,420

(22) Filed: Nov. 2, 2001

(65) Prior Publication Data

US 2002/0133083 A1 Sep. 19, 2002

(30) Foreign Application Priority Data

Mar. 16, 2001 (JP) ........................................ 2001-075720

(51) Int. Cl.[7] .............................................. A61B 5/00
(52) U.S. Cl. ........................................ 600/494; 600/495
(58) Field of Search ............................. 600/490, 493–6, 600/500

(56) References Cited

U.S. PATENT DOCUMENTS 4,484,584 A * 11/1984 Uemura ...................... 600/494
6,045,510 A * 4/2000 Ogura et al. ................ 600/494

FOREIGN PATENT DOCUMENTS

JP  B2 2-25610   6/1990
JP  A 11-4813    1/1999

* cited by examiner

*Primary Examiner*—Robert L. Nasser
(74) *Attorney, Agent, or Firm*—Oliff & Berridge, PLC

(57) ABSTRACT

An apparatus for automatically measuring a blood pressure of a living subject, including in inflatable cuff which is adapted to be wound around a portion of the subject, a cuff pulse wave including heartbeat-synchronous pulses occurring to the cuff while a pressure in the cuff is changed, a blood-pressure determining device for determining a blood pressure of the subject based on a change of respective amplitudes of the heartbeat-synchronous pulses of the cuff pulse wave, a display device which has a two-dimensional screen consisting of picture elements, and an amplitude displaying device for successively displaying, on the two-dimensional screen of the display device and while the pressure of the cuff is changed, the amplitude of each of the heartbeat-synchronous pulses of the cuff pulse wave, such that the amplitude of the each heartbeat-synchronous pulse of the cuff pulse wave is comparable with at least one prior amplitude of at least one prior heartbeat-synchronous pulse of the cuff pulse wave.

5 Claims, 6 Drawing Sheets

AUTOMATIC BLOOD-PRESSURE MEASURING APPARATUS

BACKGROUND OF THE INVENTION

1. Field of the Invention

The present invention relates to improvements of an apparatus for automatically measuring a blood pressure of a living subject.

2. Related Art Statement

There is known an oscillometric-type automatic blood-pressure measuring apparatus which automatically measures a blood pressure of a living subject according to an oscillometric method. The oscillometric-type automatic blood-pressure measuring apparatus includes an inflatable cuff which is adapted to be wound around a prescribed portion of the subject, obtains a cuff pulse wave occurring to the cuff while a pressing pressure of the cuff is slowly changed, and determines a blood pressure of the subject based on the change of respective amplitudes of respective heartbeat-synchronous pulses of the cuff pulse wave.

However, the above automatic blood-pressure measuring apparatus may measure an erroneous blood pressure of the subject, because of a physical motion of the subject during the blood-pressure measuring operation, occurrence of an arrhythmic pulse to the cuff, or noise produced by its peripheral devices. Hence, a blood-pressure measuring apparatus disclosed in Japanese Patent Document No. 2-25610 displays an array of respective amplitudes of respective heartbeat-synchronous pulses, arranged in an order of occurrence of the pulses, in a two-dimensional graph defined by a first axis indicative of pressing pressure of cuff as a first parameter and a second axis indicative of amplitude of cuff pulse wave as a second parameter, so that a degree of reliability of measured blood pressure may be judged by an operator. From the array of amplitudes being displayed, it is possible to observe a magnitude of each of the amplitudes or the manner of distribution of the amplitudes, and thereby judge the reliability of measured blood pressure. If it is judged from the displayed array of amplitudes that the reliability of measured blood pressure is insufficient, the blood-pressure measuring apparatus may be operated again to carry out another blood-pressure measuring operation and thereby obtain a reliable blood pressure.

The above-described conventional automatic blood-pressure measuring apparatus may be used in those cases in which a physical condition of a patient may abruptly change during, e.g., a surgical operation. If the condition of the patient abruptly changes, it is needed to obtain a reliable blood pressure of the patient, as soon as possible, so as to administer an appropriate treatment to the patient. However, the conventional automatic blood-pressure measuring apparatus cannot enable an operator to find an abnormality of a blood-pressure measuring operation, before the blood-pressure measuring operation is finished. Thus, there has been a demand for such an automatic blood-pressure measuring apparatus which can enable an operator to more quickly find an abnormality of a blood-pressure measuring operation.

SUMMARY OF THE INVENTION

It is therefore an object of the present invention to provide an automatic blood-pressure measuring apparatus which can enable an operator to quickly judge an abnormality of a blood-pressure measuring operation.

The Inventor has carried out extensive studies to achieve the above object, and has found the following fact: Since, in the oscillometric blood-pressure measuring method, a blood pressure is determined based on the change of respective amplitudes of respective heartbeat-synchronous pulses of a cuff pulse wave, it is possible for an operator to find an abnormality of a blood-pressure measuring operation, during that measuring operation, if each of the amplitudes of the cuff pulse wave is successively displayed during the measuring operation so that the change of the amplitudes may be observed by the operator.

Meanwhile, an automatic blood-pressure measuring apparatus disclosed in Japanese Patent Document No. 11-4813 has the function of successively displaying, during a blood-pressure measuring operation, each of respective amplitudes of respective heartbeat-synchronous pulses of a cuff pulse wave that are obtained in the measuring operation. However, this apparatus displays the amplitude of only each one heartbeat-synchronous pulse of the cuff pulse wave. Therefore, it is difficult for an operator to judge whether that amplitude is normal, or is caused by an arrhythmic pulse, or by noise produced by physical motion.

The above object has been achieved by the present invention. According to the present invention, there is provided an apparatus for automatically measuring a blood pressure of a living subject, comprising an inflatable cuff which is adapted to be wound around a portion of the subject, a cuff pulse wave including a plurality of heartbeat-synchronous pulses occurring to the cuff while a pressure in the cuff is changed; a blood-pressure determining means for determining a blood pressure of the subject based on a change of respective amplitudes of the heartbeat-synchronous pulses of the cuff pulse wave; a display device which has a two-dimensional screen consisting of a plurality of picture elements; and an amplitude displaying means for successively displaying, on the two-dimensional screen of the display device and while the pressure of the cuff is changed, the amplitude of each of the heartbeat-synchronous pulses of the cuff pulse wave, such that the amplitude of the each heartbeat-synchronous pulse of the cuff pulse wave is comparable with at least one prior amplitude of at least one prior heartbeat-synchronous pulse of the cuff pulse wave that is prior to the each heartbeat-synchronous pulse.

According to the present invention, the amplitude displaying means successively displays, on the display device and while the pressure of the cuff is changed, the amplitude of each pulse of the cuff pulse wave that is successively obtained, such that the amplitude of the each pulse of the cuff pulse wave is comparable with a prior amplitude of a prior pulse of the cuff pulse wave. If the current blood-pressure measuring operation is normal, the respective amplitudes of respective pulses of the cuff pulse wave should monotonously increase till the greatest amplitude is detected; and after the greatest amplitude is detected, the respective amplitudes of respective pulses of the cuff pulse wave should monotonously decrease. Therefore, when an operator observes that the amplitude of each pulse of the cuff pulse wave, successively displayed on the display device, has not normally changed from the amplitude of the prior pulse of the cuff pulse wave, the operator can judge, at that timing, that the current blood-pressure measuring operation is abnormal.

According to a preferred feature of the present invention, the apparatus further comprises a memory device which stores respective amplitudes of a past series of heartbeat-synchronous pulses of the cuff pulse wave that are successively obtained in a past blood-pressure measuring operation; a reference-amplitude determining means for determining a reference amplitude, based on the respective amplitudes of the heartbeat-synchronous pulses of the past series stored in the memory device; and an amplitude normalizing means for successively normalizing, based on the reference amplitude determined by the reference-amplitude determining means, the amplitude of the each of the heartbeat-synchronous pulses that are successively obtained in a current blood-pressure measuring operation, into a normalized amplitude of the each heartbeat-synchronous pulse, and the amplitude displaying means successively displays, on the two-dimensional screen of the display device and while the pressure of the cuff is changed in the current blood-pressure measuring operation, the normalized amplitudes of the each of the heartbeat-synchronous pulses, such that the normalized amplitude of the each heartbeat-synchronous pulse is comparable with at least one prior normalized amplitude of the at least one prior heartbeat-synchronous pulse prior to the each heartbeat-synchronous pulse.

In the case where an amplitude of each pulse of a cuff pulse wave that is successively obtained in a blood-pressure measuring operation is normalized, and displayed, based on an amplitude of a different pulse of the cuff pulse wave obtained in the measuring operation, for example, in the case where an amplitude of each current pulse of a cuff pulse wave is displayed with a constant magnitude by normalizing, and displaying, an amplitude of the last pulse of the cuff pulse wave based on the amplitude of the current pulse, it is difficult for an operator to judge whether each pulse of the cuff pulse wave successively obtained in the blood-pressure measuring operation is too weak to use to determine a reliable blood pressure. In contrast, according to this feature, the reference-amplitude determining means determines the reference amplitude based on the amplitudes of the past pulses, and the amplitude normalizing means successively normalizes, based on the reference amplitude, the amplitude of the each pulse successively obtained, into a normalized amplitude. And, the amplitude displaying means successively displays, on the display device, the normalized amplitude of the each pulse, such that the normalized amplitude of the each is comparable with the prior normalized amplitude of the prior pulse. Thus, the operator can easily judge whether each pulse of the cuff pulse wave successively obtained in a blood-pressure measuring operation is too small to use to determine a reliable blood pressure.

According to another preferred feature of the present invention, the apparatus further comprising a memory device which stores respective amplitudes of a past series of heartbeat-synchronous pulses of the cuff pulse wave that are successively obtained in a past blood-pressure measuring operation, such that an array of the respective amplitudes of the heartbeat-synchronous pulses of the past series can be arranged in an order of occurrence thereof to the cuff in the past blood-pressure measuring operation; and an amplitude-array displaying means for displaying, on the two-dimensional screen of the display device and while the pressure of the cuff is changed in a current blood-pressure measuring operation, the array of the respective amplitudes of the heartbeat-synchronous pulses of the past series, such that the amplitude of the each of the heartbeat-synchronous pulses of the cuff pulse wave that is successively displayed on the display device by the amplitude displaying means in the current blood-pressure measuring operation is comparable with the array of the respective amplitudes of the heartbeat-synchronous pulses of the past series that is arranged in the order of occurrence.

According to this feature, the amplitude-array displaying means displays the array of amplitudes obtained in the past blood-pressure measuring operation, such that the amplitude of each pulse of the cuff pulse wave that is successively displayed is comparable with the array of amplitudes arranged in the order of occurrence thereof. Therefore, in the case where the array of amplitudes displayed is an array of amplitudes used to provide a correct blood pressure, the operator can easily compare the amplitude of each pulse of the cuff pulse wave that is successively displayed in the current blood-pressure measuring operation, with that array of amplitudes, and judge that the current blood-pressure measuring operation is abnormal at the first time when the operator recognizes that the tendency of change of the amplitude of each pulse of the cuff pulse wave largely differs from the tendency of change of the past array of amplitudes.

According to another preferred feature, the amplitude displaying means successively displays, while the pressure of the cuff is changed, the amplitude of the each of the heartbeat-synchronous pulses of the cuff pulse wave, and the at least one prior amplitude of the at least one prior heartbeat-synchronous pulse of the cuff pulse wave, in a two-dimensional graph which is displayed on the two-dimensional screen of the display device and which is defined by a cuff-pressure axis indicative of cuff pressure as a first parameter and an amplitude axis indicative of amplitude of cuff pulse wave as a second parameter, and the apparatus further comprises a blood-pressure-symbol displaying means for displaying, when the blood pressure of the subject is determined by the blood-pressure determining means, a blood-pressure symbol indicating the thus determined blood pressure, in a vicinity of the cuff-pressure axis of the two-dimensional graph.

According to this feature, the operator can easily judge whether the current blood-pressure measuring operation is abnormal, by comparing the blood-pressure symbol with the tendency of change of the amplitudes of the cuff pulse wave.

BRIEF DESCRIPTION OF THE DRAWINGS

The above and optional objects, features, and advantages of the present invention will be better understood by reading the following detailed description of the preferred embodiments of the invention when considered in conjunction with the drawings, in which.

DETAILED DESCRIPTION OF PREFERRED EMBODIMENTS

Figure 1:
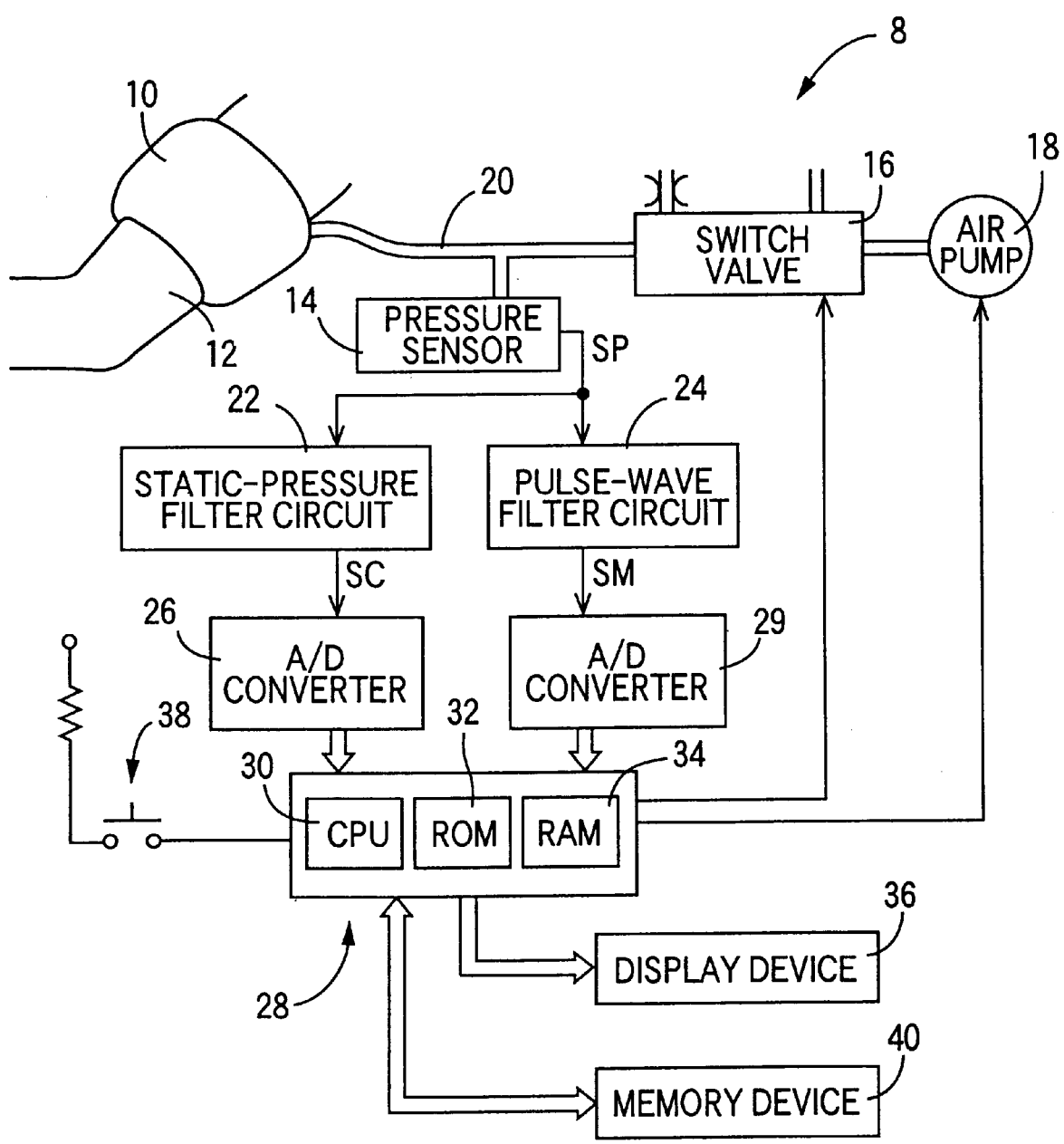
FIG. 1 is a view for explaining a construction of an automatic blood-pressure measuring apparatus to which the present invention is applied.

Hereinafter, there will be described a preferred embodiment of the present invention in detail by reference to the drawings. FIG. 1 shows a view for explaining a construction of an automatic blood-pressure measuring apparatus 8 to which the present invention is applied.

In FIG. 1, reference numeral 10 designates an inflatable cuff which includes a belt-like cloth bag and a rubber bag accommodated in the cloth bag and which is adapted to be wound around, e.g., an upper arm 12 of a patient as a living subject. The cuff 10 is connected to a pressure sensor 14, a switch valve 16, and an air pump 18 via a piping 20. The switch valve 16 is selectively placed in a pressure-supply position in which the switch valve 16 permits a pressurized air to be supplied from the air pump 18 to the cuff 10, a slow-deflation position in which the switch valve 16 permits the pressurized air to be slowly discharged from the cuff 10, and a quick-deflation position in which the switch valve 16 permits the pressurized air to be quickly discharged from the cuff 10.

The pressure sensor 14 detects an air pressure in the cuff 10, and supplies a pressure signal SP representing the detected pressure, to each of a static-pressure filter circuit 22 and a pulse-wave filter circuit 24. The static-pressure filter circuit 22 includes a low-pass filter and extracts, from the pressure signal SP, a static-pressure component contained in the pressure signal SP, i.e., a cuff-pressure signal SC representing the static pressure in the cuff 10. The cuff-pressure signal SC is supplied to a control device 28 via an analog-to-digital (A/D) converter 26.

The pulse-wave filter circuit 24 includes a band-pass filter and extracts, from the pressure signal SP, an oscillating component having predetermined frequencies, i.e., a cuff-pulse-wave signal SM. The cuff-pulse-wave signal SM is supplied to the control device 28 via an A/D converter 29. The cuff-pulse-wave signal SM represents a cuff pulse wave W, i.e., a pressure pulse wave or an oscillatory pressure wave that is produced from a brachial artery of the upper arm 12 of the patient in synchronism with the heartbeat of the patient and is propagated to the cuff 10. Therefore, the cuff pulse wave W periodically changes at the same frequency as that of the heartbeat of the patient. The A/D converter 29 periodically outputs, at a sampling period of from several milliseconds to several tens of milliseconds, a digital signal representing an instantaneous magnitude of the cuff-pulse-wave signal SM. In the case where the resolution of the A/D converter 29 is 2024 units, the A/D converter 29 converts an input (analog) signal having a magnitude of from 0 to 100 mV, into an output (digital) signal having a value of from 0 to 2024.

The control device 28 is provided by a so-called microcomputer including a central processing unit (CPU) 30, a read only memory (ROM) 32, a random access memory (RAM) 34 and an input-and-output (I/O) port, not shown. The CPU 30 processes signals according to the control programs pre-stored in the ROM 32 by utilizing the temporary-storage function of the RAM 34, and supplies drive signals via the I/O port to the switch valve 16 and the air pump 18. In addition, the CPU 30 supplies a signal representing blood-pressure values BP of the patient determined according to a prescribed algorithm, and a signal representing amplitudes A of the cuff pulse wave W, to a display device 36 having a two-dimensional screen consisting of a number of picture elements, such as a liquid-crystal panel, so that the display device 36 displays the blood-pressure values BP and the amplitudes A of the cuff pulse wave W.

The present apparatus 8 further includes a start/stop push button 38 which is operable by an operator to start or stop a blood-pressure measuring operation. Upon operation of the start/stop push button 38, a start/stop signal is supplied from the push button 38 to the control device 28. In the case where a blood-pressure measuring operation is not being carried out when the control device 28 receives the start/stop signal, the control device 28 controls the apparatus 8 to start a blood-pressure measuring operation; and in the case where a blood-pressure measuring operation is being carried out when the control device 28 receives the start/stop signal, the control device 28 controls the apparatus 8 to stop the blood-pressure measuring operation. A memory device 40 is provided by a well-known recording medium such as a magnetic disc, a magnetic tape, a volatile semiconductor memory, a non-volatile semiconductor memory, etc. The control device 28 stores, in respective prescribed memory areas of the memory device 40, an array of amplitudes and blood-pressure values BP that are determined according to a blood-pressure determining algorithm.

Figure 2:
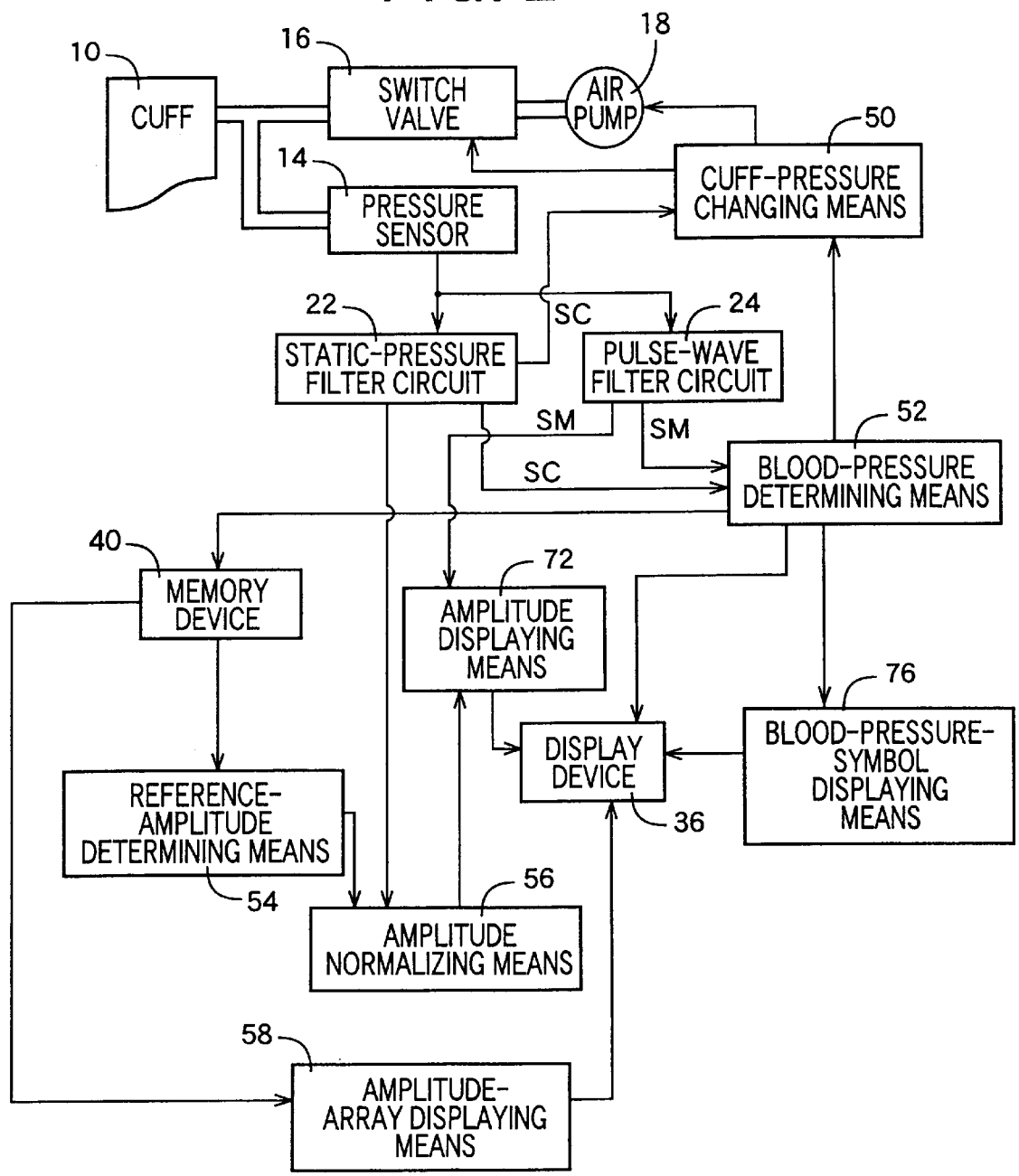
FIG. 2 is a block diagram for explaining essential functions of a control device of the apparatus of FIG. 1.

FIG. 2 is a block diagram for explaining essential functions of the control device 28. In the figure, a cuff-pressure changing means 50 operates, based on the cuff-pressure signal SC supplied from the static-pressure filter circuit 22, the air pump 18 and the switch valve 16 to quickly increase the pressing pressure of the cuff 10, i.e., the cuff pressure PC up to a prescribed target pressure $PC_M$ (e.g., 180 mmHg) which would be higher than a systolic blood-pressure value $BP_{SYS}$ of the patient and subsequently slowly decrease the cuff pressure PC at a rate of from 2 to 3 mmHg/sec. After a blood-pressure determining means 52, described below, determines blood-pressure values BP of the patient, the cuff-pressure changing means 50 operates the air pump 18 and the switch valve 16 to quickly decrease the cuff pressure PC down to an atmospheric pressure.

The blood-pressure determining means 52 determines a systolic blood-pressure value $BP_{SYS}$, a mean blood-pressure value $BP_{MEAN}$, and a diastolic blood-pressure value $BP_{DIA}$ of the patient, based on the change of the cuff-pulse-wave signal SM continuously obtained during the slow decreasing of the pressing pressure of the cuff 10 under the control of the pressure changing means 50, according to a well-known oscillometric algorithm. More specifically described, the blood-pressure determining means 52 successively determines an amplitudes $A_{(n)}$ of each of respective heartbeat-synchronous pulses $W_{(n)}$ (n=1, 2, 3 . . . ) of the cuff pulse wave W that are successively obtained while the pressing pressure of the cuff 10 is slowly decreased by the pressure changing means 50, and thereby obtains an array of amplitudes $A_{(n)}$ that are arranged in an order of occurrence of the pulses $W_{(n)}$ to the cuff 10. In addition, the blood-pressure determining means 52 determines, as the systolic blood-pressure value $BP_{SYS}$, a value of the cuff pressure PC at the time when the rate of change of the amplitudes $A_{(n)}$ increases so largely that the rate of change is greater than a prescribed positive reference value; determines, as the diastolic blood-pressure value $BP_{DIA}$, a value of the cuff pressure PC at the time when the rate of change of the amplitudes $A_{(n)}$ decreases so largely that the rate of change is smaller than a prescribed negative reference value; and determines, as the mean blood-pressure value $BP_{MEAN}$, a value of the cuff pressure PC at the time when the greatest one of the amplitudes $A_{(n)}$ is obtained. The blood-pressure determining means 52 operates the display device 36 to display the thus determined systolic blood-pressure value $BP_{SYS}$, etc., and operates the memory device 40 to store, in the prescribed memory area thereof, the array of amplitudes $A_{(n)}$ such that each of the amplitudes $A_{(n)}$ is associated with the cuff-pressure value PC at the time of occurrence of the each amplitude $A_{(n)}$ to the cuff 10.

A reference-amplitude determining means 54 determines a reference amplitude Ast based on at least one array of amplitudes $A_{(n)}$ obtained, and stored in the memory device 40, in at least one past blood-pressure measuring operation. For example, the reference-amplitude determining means 54 determines, as the reference amplitude Ast, the greatest one Amax of the amplitudes $A_{(n)}$ obtained in the last blood-pressure measuring, operation, or an average of the amplitudes $A_{(n)}$ obtained in the last blood-pressure measuring operation.

An amplitude normalizing means 56 successively normalizes, based on the reference amplitude Ast determined by the reference-amplitude determining means 54, the amplitude $A_{(n)}$ of each of the respective pulses $W_{(n)}$ of the cuff pulse wave represented by the pulse-wave signal SM supplied from the pulse-wave filter circuit 24 during the slow decreasing of the cuff pressure PC, into a normalized amplitude $AF_{(n)}$. More specifically described, the amplitude normalizing means 56 successively determines an amplitude $A_{(n)}$ of each of the respective pulses $W_{(n)}$ of the cuff pulse wave, and determines a normalized amplitude $AF_{(n)}$ based on the thus determined amplitude $A_{(n)}$ according to the following expression (1):

$$AF_{(n)} = A_{(n)}/Ast \quad (1)$$

Figure 3:
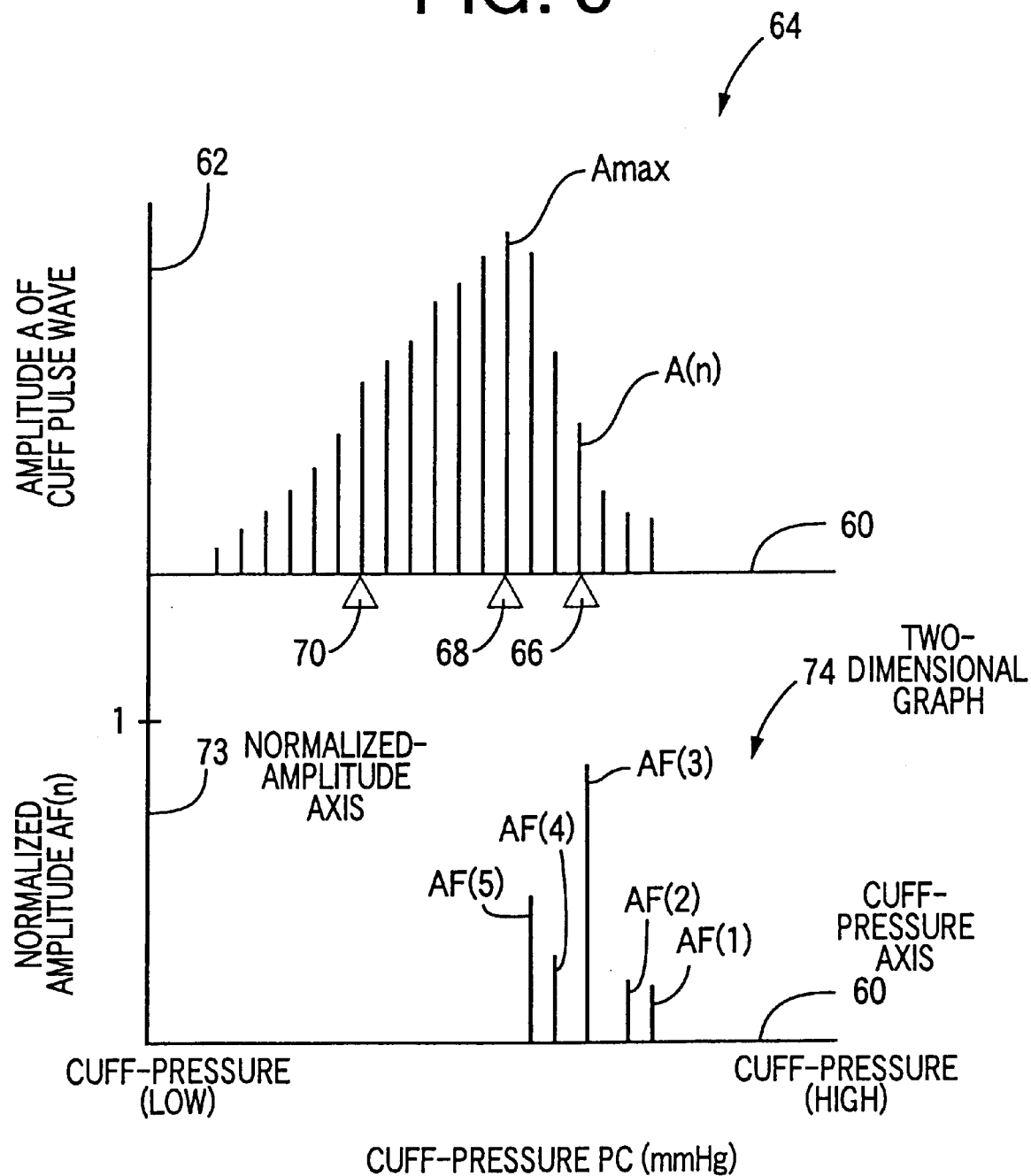
FIG. 3 is a graph showing respective examples of an array of amplitudes obtained in a past blood-pressure measuring operation and normalized amplitudes $AF_{(n)}$ obtained a current blood-pressure measuring operation that are displayed such that each of the normalized amplitudes $AF_{(n)}$ is comparable with the array of amplitudes.

An amplitude-array displaying means 58 displays an array of amplitudes $A_{(n)}$ obtained, and stored in the memory device 40, in a past blood-pressure measuring operation, such that the array of amplitudes $A_{(n)}$, arranged in the order of occurrence thereof to the cuff 10, is comparable with each of the amplitudes $A_{(n)}$ that is successively displayed by an amplitude displaying means 72, described below, in the current blood-pressure measuring operation. An upper half portion of FIG. 3 shows an example of the array of amplitudes $A_{(n)}$ displayed by the amplitude-array displaying means 58. In the upper half portion of FIG. 3, each of the amplitudes $A_{(n)}$ of this array is indicated at a bar in a two-dimensional graph 64 that is defined by a cuff-pressure axis 60 indicative of cuff pressure PC as a first parameter and an amplitude axis 62 indicative of amplitude Am of cuff pulse wave $W_{(n)}$ as a second parameter. Under the cuff-pressure axis 60, three triangular blood-pressure symbols 66, 68, 70 indicate the systolic blood-pressure value $BP_{SYS}$, mean blood-pressure value $BP_{MEAN}$, and diastolic blood-pressure value $BP_{DIA}$, respectively, that are determined according to the oscillometric algorithm. This array of amplitudes $A_{(n)}$ is one obtained in a normal blood-pressure measuring operation.

The amplitude displaying means 72 successively displays, on the display device 36 and during the slow decreasing of the cuff pressure PC, the amplitude $A_{(n)}$ of each of the pulses $W_{(n)}$ of the cuff pulse wave that is successively obtained by the pulse-wave filter circuit 24 during the slow decreasing of the cuff pressure PC, such that the amplitude $A_{(n)}$ of the each pulse $W_{(n)}$ is comparable with at least one prior amplitude $A_{(n-m)}$ (m=1, 2, 3, ...) of at least one prior pulse $W_{(n-m)}$ of the cuff pulse wave that is prior to the each pulse $W_{(n)}$. In the present automatic blood-pressure measuring apparatus 8, the amplitude displaying means 72 successively displays, on the display device 36, the normalized amplitude $AF_{(n)}$ provided by the amplitude normalizing means 56 based on the amplitude $A_{(n)}$ of the each pulse $W_{(n)}$. The at least one prior amplitude $A_{(n-m)}$ (or at least one prior normalized amplitude $AF_{(n-m)}$) of the at least one prior pulse $W_{(n-m)}$, displayed with the amplitude $A_{(n)}$ (or the normalized amplitude $AF_{(n)}$), includes the last amplitude $A_{(n-1)}$ (or the last normalized amplitude $AF_{(n-1)}$) of the last pulse $W_{(n-1)}$, and preferably includes all the prior amplitudes $A_1, A_2, A_3, \ldots, A_{(n-1)}$ (or all the prior normalized amplitudes $AF_1, AF_2, AF_3, \ldots, AF_{(n-1)}$).

A lower half portion of FIG. 3 shows an example of each of the normalized amplitudes $AF_{(n)}$ that is successively displayed by the amplitude displaying means 72. In the lower half portion of FIG. 3, each of the amplitudes $AF_{(n)}$ is indicated at a bar in a two-dimensional graph 74 that is defined by the cuff-pressure axis 60 shared with the two-dimensional graph 64, and a normalized-amplitude axis 73 indicative of normalized amplitude $AF_{(n)}$ as a second parameter. In the example shown in the lower half portion of FIG. 3, the current normalized amplitude $AF_{(n)}$ is displayed with all the prior normalized amplitudes $AF_{(1)}, AF_{(2)}, AF_{(3)}, \ldots, AF_{(n-1)}$. In this example, the third normalized amplitude $AF_{(3)}$ is significantly greater than the second normalized amplitude $AF_{(2)}$, and a difference between respective cuff-pressure values PC corresponding to the second and third normalized amplitude $AF_{(2)}, AF_{(3)}$ is apparently greater than a difference between respective cuff-pressure values PC corresponding to the first and second normalized amplitude $AF_{(1)}, AF_{(2)}$. Therefore, an operator, such as a doctor, can judge, upon displaying of the third normalized amplitude $AF_{(3)}$ on the display device 36, that the third pulse $W_{(3)}$ providing the third normalized amplitude $AF_{(3)}$ is an arrhythmic pulse, and that even if the current blood-pressure measuring operation may be continued, blood-pressure values BP could not be determined, or unreliable blood-pressure values BP, would be determined, if could be. Since, in the example shown in the lower half portion of FIG. 3, the fourth normalized amplitude $AF_{(4)}$ following the third normalized amplitude $AF_{(3)}$ is significantly smaller than the third normalized amplitude $AF_{(3)}$, the operator can more clearly judge, when the fourth normalized amplitude $AF_{(4)}$ is displayed on the display device 36, that the current blood-pressure measuring operation is abnormal. In addition, in the examples shown in FIG. 3, the upper two-dimensional graph 64 and the lower two-dimensional graph 74 share the same cuff-pressure axis 60 as the axis of abscissa, so that each of the normalized amplitudes $AF_{(n)}$ that is successively displayed in the current blood-pressure measuring operation is easily comparable with the array of amplitudes obtained in the last blood-pressure measuring operation. Therefore, if a tendency of change of the normalized amplitudes $AF_{(n)}$ displayed in the current blood-pressure measuring largely differs from a tendency of change of the array of amplitudes displayed in the upper two-dimensional graph 64, the operator can judge that the current blood-pressure measuring operation is abnormal.

Figure 4:
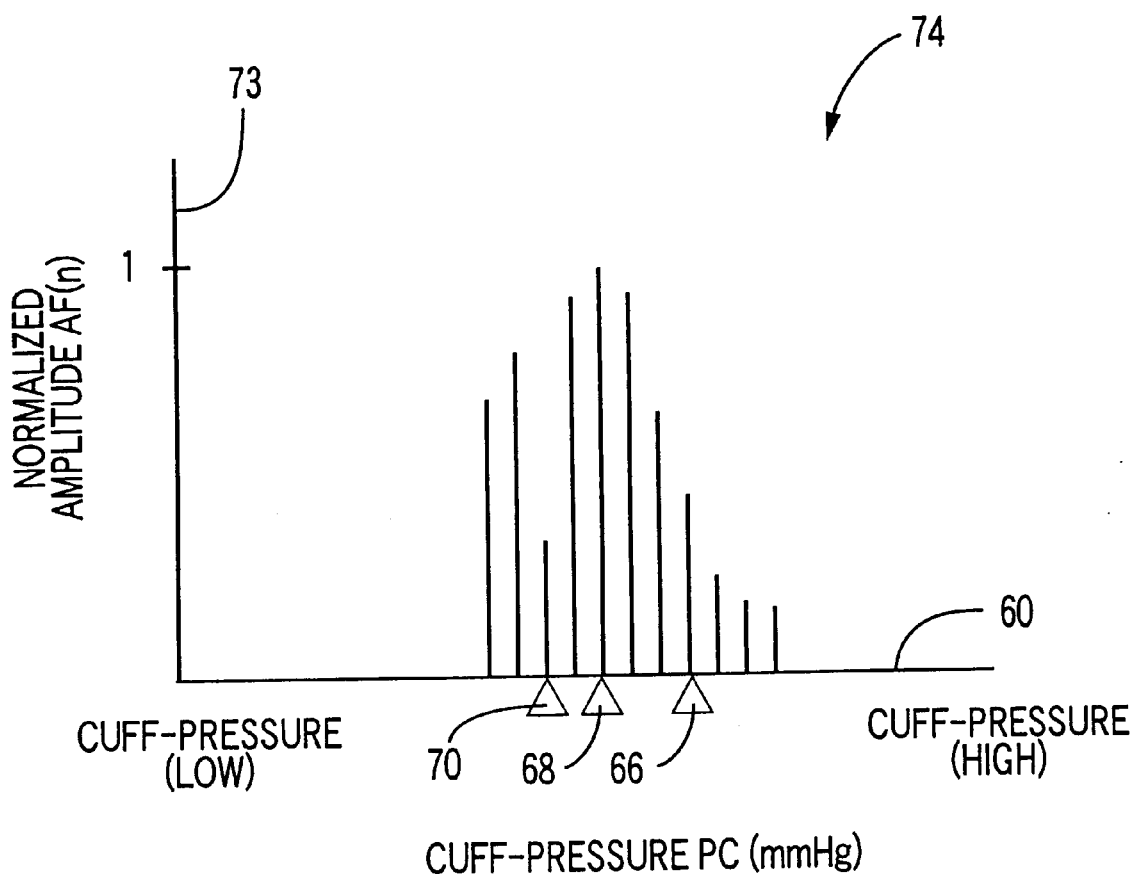
FIG. 4 is a graph showing a different example of current normalized amplitudes $AF_{(n)}$ being successively displayed, than the example shown in a lower half portion of the graph of FIG. 3.

A blood-pressure-symbol displaying means 76 displays, when a blood-pressure value BP is determined by the blood-pressure determining means 52 according to the oscillometric algorithm, a blood-pressure symbol indicating the thus determined blood-pressure value BP, in the vicinity of the cuff-pressure axis 60 of the two-dimensional graph 64, at a position corresponding to the pressure value BP on the pressure axis 60. FIG. 4 shows, in the two-dimensional graph 74, a different example of normalized amplitudes $AF_{(n)}$ displayed by the amplitude displaying means 72, than the example shown in the lower half portion of FIG. 3. FIG. 4 shows examples of the blood-pressure symbols displayed by the blood-pressure-symbol displaying means 76, i.e., the same triangular blood-pressure symbols 66, 68, 70 as those displayed in the upper two-dimensional graph 64 of FIG. 3. If, in the current blood-pressure measuring operation, the triangular blood-pressure symbol 70 indicating the diastolic blood-pressure value $BP_{DIA}$ is displayed in the two-dimensional graph 74, then the operator can judge, in the current blood-pressure measuring operation, that a cuff-pressure value PC at the time when the cuff pulse wave temporarily shows a weak or small amplitude is determined as the diastolic blood-pressure value $BP_{DIA}$ but this diastolic blood-pressure value $BP_{DIA}$ is an erroneous measurement, because that small amplitude is followed by significantly greater amplitudes $A_{(n)}$.

Figure 5:
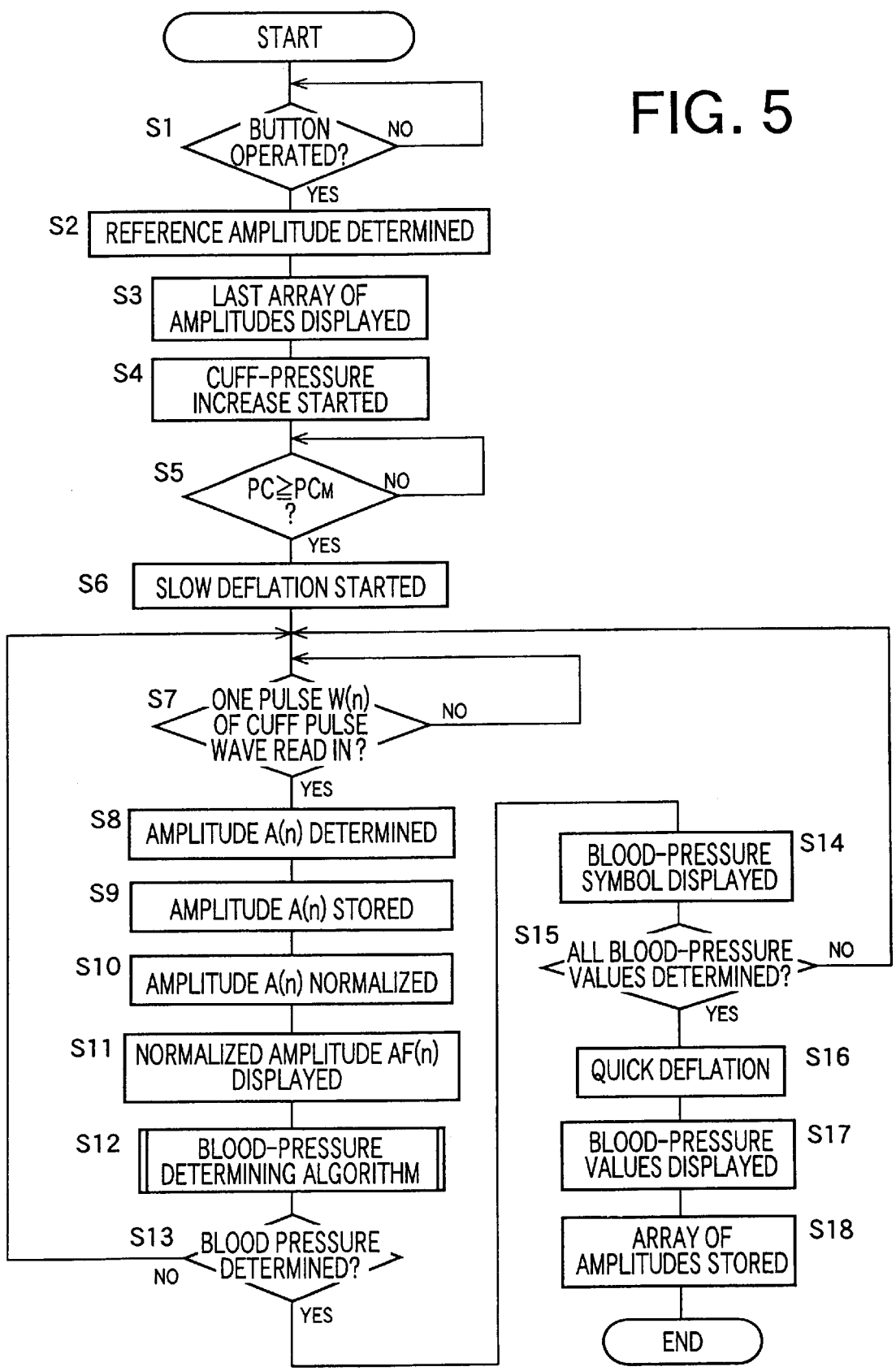
FIG. 5 is a flow chart representing a control program according to which the control device of FIG. 2 is operated.

FIG. 5 is a flow chart representing the essential control functions of the control device 28 shown in FIG. 2. In FIG. 5, first, the control device 28 carries out Step S1 (hereinafter, "Step" is omitted, if appropriate) to judge whether when the start/stop push button 38 is operated by the operator and accordingly the control device 28 has received the start/stop signal from the button 38. If a negative judgment is made at S1, S1 is repeated. On the other hand, if a positive judgment is made at S1, the control goes to S2 corresponding to the reference amplitude determining means 54. At S2, the control device 28 determines, as the reference amplitude Ast, the greatest one Amax of all the amplitudes $A_{(n)}$ obtained in the last blood-pressure measuring operation and stored in the memory device 40. However, in an initial blood-pressure measuring operation in which no amplitudes $A_{(n)}$ have been stored in the memory device 40, a standard amplitude which is experimentally obtained in advance is determined as the reference amplitude Ast.

Next, the control goes to S3 corresponding to the amplitude-array displaying means 58. At S3, the control device 28 displays, on the display device 36, an array of amplitudes stored in the memory device 40 at S18, described later, in the last control cycle according to this routine, i.e., in the last blood-pressure measuring operation, as shown in the upper half portion of FIG. 3. If the operator judges, during a blood-pressure measuring operation, that the blood-pressure measuring operation is abnormal, he or she will abort the blood-pressure measuring operation. Therefore, only an array of amplitudes obtained in a normal blood-pressure measuring operation is stored in the memory device 40, and is displayed at S3.

Then, at S4, the control device 28 starts the air pump 18 and switches the switch valve 16 to its pressure-supply position, so that the pressing pressure of the cuff 10, i.e., the cuff pressure PC is quickly increased. At S5, the control device 28 judges whether the cuff pressure PC has reached a prescribed target pressure $PC_M$, e.g., 180 mmHg, that is higher than a standard systolic blood pressure $BP_{SYS}$.

If a negative judgment is made at S5, S5 is repeated till a positive judgment is made. Thus, the increasing of the cuff pressure PC is continued. Meanwhile, if the cuff pressure PC is increased and a positive judgment is made at S5, the control goes to 6 to stop the air pump 18 and switch the switch valve 16 to its slow-deflation position, so that the cuff pressure PC is slowly decreased at a prescribed rate of from 2 to 3 mmHg/sec.

At S7, the control device 28 judges whether the control device 28 has gathered a sufficient amount of data points of the pulse-wave signal SM, periodically supplied at a prescribed sampling period from the A/D converter 29, that enables the control device 28 to determine an amplitude $A_{(n)}$ of one heartbeat-synchronous pulse $W_{(n)}$ of the cuff pulse wave. For example, a positive judgment is made when the control device 28 has gathered data points corresponding to a rising point and peak point of a pulse.

Then, at S8, the control device 28 determines the amplitude $A_{(n)}$ of the one pulse $W_{(n)}$ of the cuff pulse wave gathered at S7. The amplitude A(n) is determined as a difference between respective magnitudes of the pulse-wave signal SM that correspond to the rising point and the peak point of the one pulse. Then, at S9, the control device 28 temporarily stores, in the RAM 34, the amplitude $A_{(n)}$ determined at S8 and a cuff-pressure value PC at the time of detection of the peak point of the one pulse $W_{(n)}$.

The control goes to S10 corresponding to the amplitude normalizing means 56. At S10, the control device 28 determines a normalized amplitude $AF_{(n)}$ based on the reference amplitude Ast determined at S2 and the amplitude A. determined at S8 according to the previously-explained expression (1).

Then, the control goes to S11 corresponding to the amplitude displaying means 72. At S11, the control device 28 operates the display device 36 to display the normalized amplitude $AF_{(n)}$ determined at S10, in the form of a bar, as shown in the lower two-dimensional graph 74 of FIG. 3.

Next, the control goes to S12, corresponding to the blood-pressure determining means 52, where the blood-pressure determining algorithm is carried out. More specifically described, at S12, the control device 28 determines a systolic blood pressure $BP_{SYS}$, a mean blood pressure $BP_{MEAN}$, and a diastolic blood pressure $BP_{DIA}$ of the patient, based on a change of the respective amplitudes $A_{(n)}$ of the pulses $W_{(n)}$ of the cuff pulse wave, determined at S8, according to a well-known oscillometric blood-pressure determining algorithm.

At S13, the control device 28 judges whether any one of the systolic blood pressure $BP_{SYS}$, the mean blood pressure $BP_{MEAN}$, and the diastolic blood pressure $BP_{DIA}$ has been determined, and identifies which one of the three blood-pressure values has been determined. If a negative judgment is made at S13, the control goes back to S7 and the following steps to detect more pulses $W_{(n)}$ of the cuff pulse wave, determine respective amplitudes $A_{(n)}$ of the detected pulses $W_{(n)}$, normalize the determined amplitudes $A_{(n)}$ into respective normalized amplitudes $AF_{(n)}$, and successively display each of the normalized amplitudes $AF_{(n)}$ on the display device 36 while the cuff pressure PC is slowly decreased.

Meanwhile, if a positive judgment is made at S13, the control goes to S14 corresponding to the blood-pressure-symbol displaying means 76. At S14, the control device 28 displays, at a position right below the cuff-pressure axis 60 of the two-dimensional graph 74 displayed on the display device 36, one of the blood-pressure symbols 66, 68, 70, shown in FIG. 4, that corresponds to the one blood-pressure value identified at S13.

Then, at S15, the control device 28 judges whether all of the three blood-pressure values BP have been determined. Since the diastolic blood pressure $BP_{DIA}$ is last determined in the systolic blood pressure $BP_{SYS}$, the mean blood pressure $BP_{MEAN}$, and the diastolic blood pressure $BP_{DIA}$, the control device 28 judges whether the diastolic blood pressure $BP_{DIA}$ has been determined. In an initial time period, a negative judgment is made at S15, and the control goes to S7 and the following steps.

Meanwhile, if a positive judgment is made at S15, the control goes to S16 to switch the switch valve 16 to its quick-deflation position so that the air in the cuff 10 is quickly discharged and the pressing pressure of the cuff 10 is released. Thus, in the flow chart of FIG. 5, S4 to S6 and S16 correspond to the cuff-pressure changing means 50.

Then, at S17, the control device 28 digitally displays, on the display device 36, the systolic blood pressure $BP_{SYS}$, the mean blood pressure $BP_{MEAN}$, and the diastolic blood pressure $BP_{DIA}$, all determined at S12. At S18, the control device 28 stores, in the prescribed memory area of the memory device 40, the array or series of amplitudes $A_{(n)}$ successively and temporarily stored in the RAM 34 at S9, as a result of repetition of S7 to S15, and the current control cycle according to this routine is finished. If the start/stop push button 38 is operated, in the current control cycle according to this routine, by the operator who has judged from the normalized amplitudes $AF_{(n)}$ successively displayed on the display device 28 that the current blood-pressure measuring operation is abnormal, the current control cycle is aborted.

In the illustrated embodiment in which the above-described flow chart is employed, at S11 (the amplitude displaying means 72), the control device 28 successively displays, while the cuff pressure PC is slowly decreased, each normalized amplitude $AF_{(n)}$ obtained from each amplitude $A_{(n)}$ of each pulse $W_{(n)}$ of the cuff pulse wave that is successively obtained, such that the each normalized amplitude $AF_{(n)}$ is comparable with one or more prior normalized amplitude $AF_{(n-m)}$ prior to the each normalized amplitude $AF_{(n)}$. When the operator observes that the each normalized amplitude $AF_{(n)}$ displayed on the display device 36 has not normally changed from the prior normalized amplitude $AF_{(n-m)}$, he or she can judge, at that timing, that the current blood-pressure measuring operation is abnormal.

In addition, in the embodiment in which the flow chart is employed, at S2 (the reference-amplitude determining means 54), the greatest amplitude Amax obtained in the last blood-pressure measuring operation is determined as the reference amplitude Ast and, at S10 (the amplitude normalizing means 56), the amplitude $A_{(n)}$ of each pulse $W_{(n)}$ of the cuff pulse wave is normalized, based on the reference amplitude Ast, into a normalized amplitude $AF_{(n)}$. At S11 (the amplitude displaying means 72), each normalized amplitude $AF_{(n)}$ is successively displayed on the display device 36 such that the each normalized amplitude $AF_{(n)}$ is comparable with one or more prior normalized amplitude $AF_{(n-m)}$ obtained prior to the each normalized amplitude $AF_{(n)}$. Thus, the operator can easily judge whether the amplitude $A_{(n)}$ of each of the pulses $W_{(n)}$ of the cuff pulse wave that is successively obtained is too small or too great to use to determine a reliable blood pressure BP.

In addition, in the embodiment in which the flow chart is employed, at S3 (the amplitude-array displaying means 58), the display device 36 displays the array of amplitudes $A_{(n)}$ obtained in the last blood-pressure measuring operation, such that the array of amplitudes $A_{(n)}$, arranged in the order of occurrence thereof, is comparable with each of the normalized amplitudes $AF_{(n)}$ that is successively displayed. Therefore, when the operator compares the array of amplitudes $A_{(n)}$ with each of the normalized amplitudes $AF_{(n)}$ that is successively displayed in the current blood-pressure measuring operation, and observes that the tendency of change of the each normalized amplitude $AF_{(n)}$ largely differs from the tendency of change of the array of amplitudes $A_{(n)}$, he or she can judge already at that timing that the current blood-pressure measuring operation is abnormal.

In addition, in the embodiment in which the flow chart is employed, at S14 (the blood-pressure-symbol displaying means 76), the display device 36 displays, when each of the three blood-pressure values BP is determined, a corresponding one of the three blood-pressure symbols 66, 68, 70, at a position right below the each pressure value on the cuff-pressure axis 60 of the two-dimensional graph 74. Therefore, the operator can easily compare the blood-pressure symbols 66, 68, 70 with the tendency of change of the normalized amplitudes $AF_{(n)}$ and thereby judge whether the current blood-pressure measuring operation is abnormal.

While the present invention has been described in its preferred embodiment by reference to the drawings, it is to be understood that the invention may otherwise be embodied.

For example, in the illustrated embodiment, the amplitude displaying means 72 successively displays a bar representing each amplitude $A_{(n)}$. However, it is possible to display each amplitude $A_{(n)}$ in a different manner, for example, display a polygonal graph representing respective amplitudes $A_{(n)}$.

Figure 6:
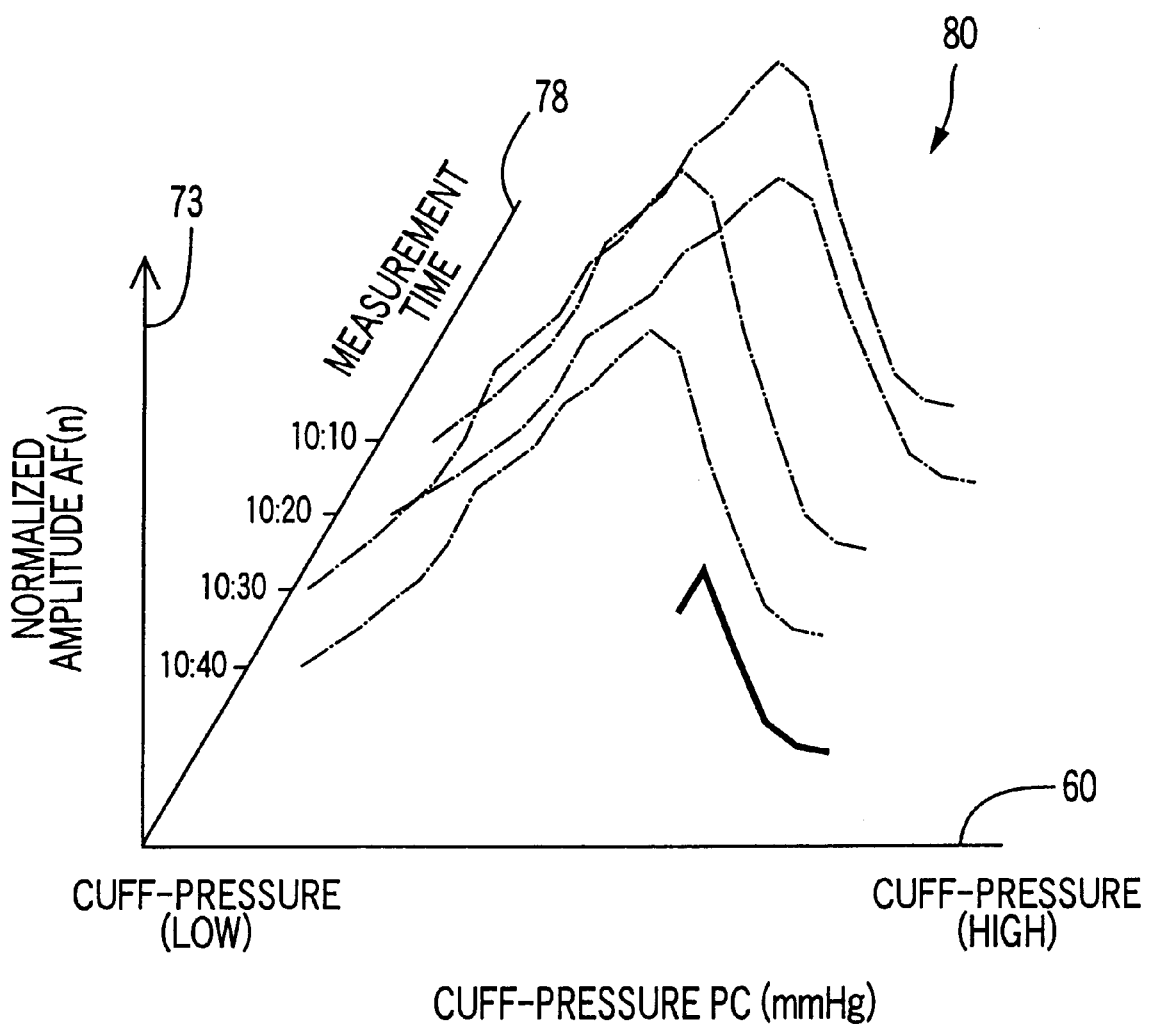
FIG. 6 is a graph showing a different manner in which current normalized amplitudes $AF_{(n)}$ are successively displayed, than the manner shown in FIG. 3.

In addition, in the illustrated embodiment, the amplitude-array displaying means 58 displays the array of amplitudes obtained in the last blood-pressure measuring operation, as the array of amplitudes to be compared with each of the amplitudes $A_{(n)}$ obtained in the current blood-pressure measuring operation. However, as shown in FIG. 6, it is possible to display a plurality of arrays of amplitudes obtained in the last blood-pressure measuring operation and one or more past blood-pressure measuring operations prior to the last operation. In FIG. 6, the display device 36 displays, in a three-dimensional graph 80 defined by the cuff-pressure axis 60, the normalized-amplitude axis 73, and a measurement-time axis 78 indicative of measurement time as a third parameter, the arrays of amplitudes, indicated at one-dot chain line, obtained in two or more past blood-pressure measuring operations and the array of amplitudes $A_{(n)}$, indicated at solid line, obtained in the current blood-pressure measuring operation.

The illustrated automatic blood-pressure measuring apparatus 8 starts a blood-pressure measuring operation when the start/stop push button 38 is operated. However, the apparatus 8 may be modified such that the apparatus 8 automatically starts a blood-pressure measuring operation at a prescribed blood-pressure-measure period.

Moreover, in the illustrated embodiment, the amplitude displaying means 72 successively displays each normalized amplitude $AF_{(n)}$ in the two-dimensional graph 74 defined by the cuff-pressure axis 60 and the normalized amplitude axis 73. However, since the cuff pressure PC is slowly decreased at a constant rate, respective values of the cuff pressure PC correspond, one by one, to respective times during the slow decreasing of the cuff pressure PC. Therefore, the cuff-pressure axis 60 may be replaced with a time axis.

It is to be understood that the present invention may be embodied with other changes, improvements, and modifications that may occur to a person skilled in the art without departing from the spirit and scope of the invention defined in the appended claims.

What is claimed is:

1. An apparatus for automatically measuring a blood pressure of a living subject, comprising:

an inflatable cuff which is adapted to be wound around a portion of the subject for obtaining a cuff pulse wave including a plurality of heartbeat-synchronous pulses occurring to the cuff while a pressure in the cuff is changed;

a blood-pressure determining means for determining a blood pressure of the subject based on a change of respective amplitudes of the heartbeat-synchronous pulses of the cuff pulse wave successively obtained by the inflatable cuff while the pressure in the cuff is changed;

a display device which has a two-dimensional screen consisting of a plurality of picture elements; and an amplitude displaying means for successively displaying, on the two-dimensional screen of the display device and while the pressure of the cuff is changed in the current blood-pressure measuring operation, the amplitude of each of the heartbeat-synchronous pulses of the cuff pulse wave successively obtained by the inflatable cuff while the pressure in the cuff is changed, such that the amplitude of said each heartbeat-synchronous pulse of the cuff pulse wave is comparable with at least one prior amplitude of at least one prior heartbeat-synchronous pulse of the cuff pulse wave that is prior to said each heartbeat-synchronous pulse.

2. An apparatus according to claim 1, further comprising:

a memory device which stores respective amplitudes of a past series of heartbeat-synchronous pulses of the cuff pulse wave that are successively obtained in a past blood-pressure measuring operation;

a reference-amplitude determining means for determining a reference amplitude, based on the respective amplitudes of the heartbeat-synchronous pulses of the past series stored in the memory device; and an amplitude normalizing means for successively normalizing, based on the reference amplitude determined by the reference-amplitude determining means, the amplitude of said each of the heartbeat-synchronous pulses that is successively obtained in a current blood-pressure measuring operation, into a normalized amplitude of said each heartbeat-synchronous pulse, wherein the amplitude displaying means successively displays, on the two-dimensional screen of the display device and while the pressure of the cuff is changed in the current blood-pressure measuring operation, the normalized amplitudes of said each of the heartbeat-synchronous pulses, such that the normalized amplitude of said each heartbeat-synchronous pulse is comparable with at least one prior normalized amplitude of said at least one prior heartbeat-synchronous pulse prior to said each heartbeat-synchronous pulse.

3. An apparatus according to claim 1, further comprising:

a memory device which stores respective amplitudes of a past series of heartbeat-synchronous pulses of the cuff pulse wave that are successively obtained in a past blood-pressure measuring operation, such that an array of the respective amplitudes of the heartbeat-synchronous pulses of the past series can be arranged in an order of occurrence thereof to the cuff in the past blood-pressure measuring operation; and an amplitude-array displaying means for displaying, on the two-dimensional screen of the display device and while the pressure of the cuff is changed in a current blood-pressure measuring operation, the array of the respective amplitudes of the heartbeat-synchronous pulses of the past series, such that the amplitude of said each of the heartbeat-synchronous pulses of the cuff pulse wave that is successively displayed on the display device by the amplitude displaying means in the current blood-pressure measuring operation is comparable with the array of the respective amplitudes of the heartbeat-synchronous pulses of the past series that is arranged in the order of occurrence.

4. An apparatus according to claim 1, wherein the amplitude displaying means successively displays, while the pressure of the cuff is changed, the amplitude of said each of the heartbeat-synchronous pulses of the cuff pulse wave, and said at least one prior amplitude of said at least one prior heartbeat-synchronous pulse of the cuff pulse wave, in a two-dimensional graph which is displayed on the two-dimensional screen of the display device and which is defined by a cuff-pressure axis indicative of cuff pressure as a first parameter and an amplitude axis indicative of amplitude of cuff pulse wave as a second parameter, and wherein the apparatus further comprises a blood-pressure-symbol displaying means for displaying, when the blood pressure of the subject is determined by the blood-pressure determining means, a blood-pressure symbol indicating the thus determined blood pressure, in a vicinity of the cuff-pressure axis of the two-dimensional graph.

5. An apparatus according to claim 1, further comprising:

a pressure changing device which changes the pressure of the cuffs;

a pressure sensor which detects the pressure of the cuff changed by the pressure changing device; and a cuff-pulse-wave detecting device which detects the cuff pulse wave occurring to the cuff when the pressure of the cuff is changed by the pressure changing device.

* * * * *